United States Patent
Moser et al.

(10) Patent No.: US 11,337,978 B2
(45) Date of Patent: May 24, 2022

(54) STABLE LYOPHILISATES COMPRISING 5,10-METHYLENE-(6R)-TETRAHYDROFOLIC ACID

(71) Applicant: Merck Patent GmbH, Darmstadt (DE)

(72) Inventors: Rudolf Moser, Schaffhausen (CH); Viola Groehn, Dachsen (CH); Thomas Ammann, Marthalen (CH)

(73) Assignee: Merck Patent GmbH, Darmstadt (DE)

(*) Notice: Subject to any disclaimer, the term of this patent is extended or adjusted under 35 U.S.C. 154(b) by 0 days.

(21) Appl. No.: 16/638,528

(22) PCT Filed: Aug. 15, 2018

(86) PCT No.: PCT/EP2018/072077
§ 371 (c)(1),
(2) Date: Feb. 12, 2020

(87) PCT Pub. No.: WO2019/034673
PCT Pub. Date: Feb. 21, 2019

(65) Prior Publication Data
US 2020/0368236 A1    Nov. 26, 2020

(30) Foreign Application Priority Data
Aug. 16, 2017 (EP) .................................. 17186518

(51) Int. Cl.
| | | |
|---|---|---|
| *A61K 31/498* | (2006.01) | |
| *A61P 35/00* | (2006.01) | |
| *A61K 31/519* | (2006.01) | |
| *A61K 9/19* | (2006.01) | |
| *A61K 47/12* | (2006.01) | |

(52) U.S. Cl.
CPC .............. *A61K 31/519* (2013.01); *A61K 9/19* (2013.01); *A61K 47/12* (2013.01)

(58) Field of Classification Search
CPC ............................. A61K 31/498; A61P 35/00
USPC .......................................................... 514/250
See application file for complete search history.

(56) References Cited

U.S. PATENT DOCUMENTS

| | | | |
|---|---|---|---|
| 9,180,128 B2 | 11/2015 | Moser et al. | |
| 9,993,464 B2 | 6/2018 | Kamm et al. | |
| 10,059,710 B2* | 8/2018 | Moser ................. | A61K 9/0019 |
| 10,570,134 B2* | 2/2020 | Moser ................. | A61K 31/519 |
| 2002/0103126 A1 | 8/2002 | Rodel et al. | |
| 2007/0099866 A1 | 5/2007 | Moser et al. | |
| 2009/0221594 A1 | 9/2009 | Chen et al. | |
| 2016/0030573 A1 | 2/2016 | Moser et al. | |

FOREIGN PATENT DOCUMENTS

| | | |
|---|---|---|
| CN | 104490887 A | 4/2015 |
| EA | 025572 B1 | 1/2017 |
| WO | 2004/112761 A2 | 12/2004 |
| WO | 2007/064968 A2 | 6/2007 |

OTHER PUBLICATIONS

International Search Report dated Sep. 17, 2018 issued in corresponding PCT/EP2018/072077 application (3 pages).
Office Action in corresponding Indian Application No. 202037010510 dated Aug. 30, 2021 (pp. 1-6).
Office Action in corresponding Russian Patent Application No. 2020 110 073 dated Jan. 24, 2022 (pp. 1-4).

* cited by examiner

*Primary Examiner* — Raymond J Henley, III
(74) *Attorney, Agent, or Firm* — Millen, White, Zelano and Branigan, P.C.; Harry B. Shubin

(57) ABSTRACT

The present invention is directed to stable lyophilisates comprising 5,10-methylene-(6R)-tetrahydrofolic acid or a pharmaceutically acceptable salt thereof and a dicarboxylic acid, or a salt thereof, as well as, a processes of obtaining the same, and the use of such products.

11 Claims, 1 Drawing Sheet

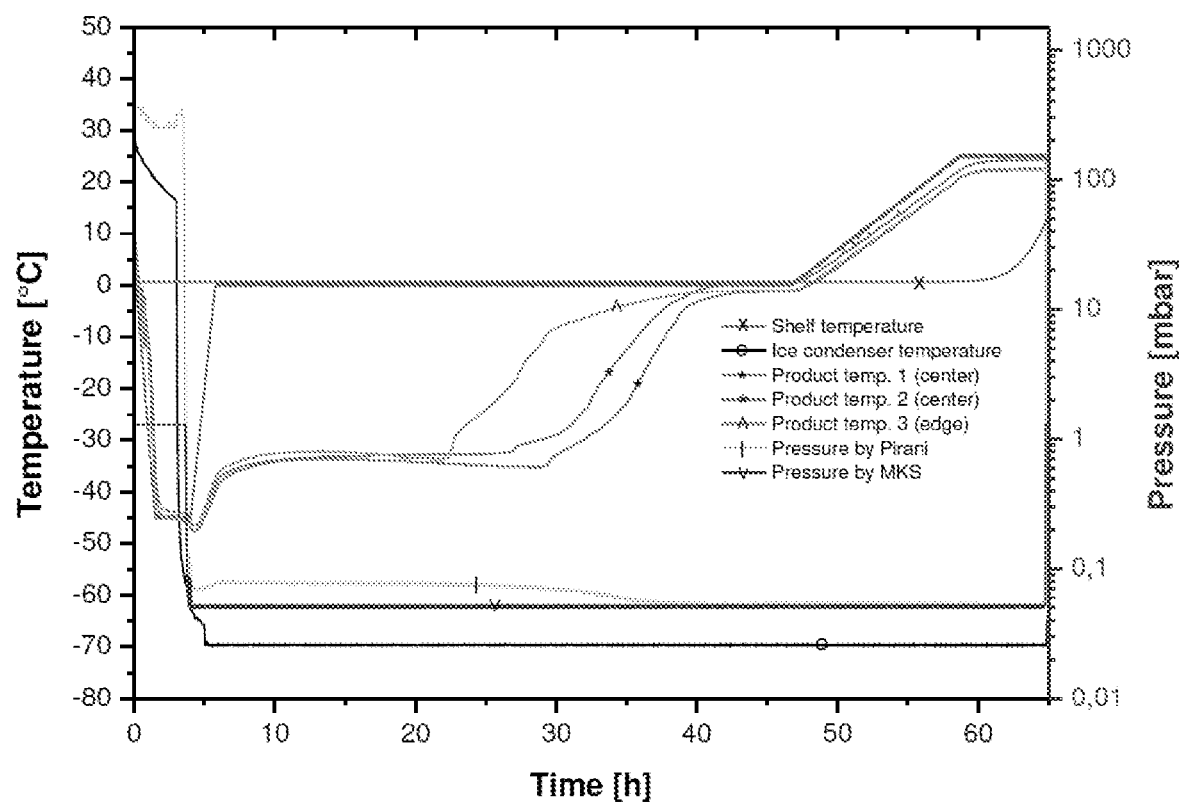
Online data recorded during a lyophilization

STABLE LYOPHILISATES COMPRISING 5,10-METHYLENE-(6R)-TETRAHYDROFOLIC ACID

The present invention directed towards stable lyophilisates comprising 5,10-methylene-(6R)-tetrahydrofolic acid [5,10-(6R)—$CH_2$-THF], or a pharmaceutically acceptable salt thereof, and a dicarboxylic acid, or a salt thereof.

As used herein, 5,10-$CH_2$-(6R)-THF refers to 5,10-methylenetetrahydrofolic acid in its naturally occurring isomeric form (N-[4-[(6aR)-3-amino-1,2,5,6,6a,7-hexahydro-1-oxoimidazo[1,5-f]pteridin-8(9H)-yl]benzoyl]-L-glutamic acid), wherein the chiral centers at C6 of the pteridine ring and the α-carbon of the glutamic acid moiety are in their naturally occurring configuration.

5,10-methylenetetrahydrofolic acid in combination with 5-fluorouracil (5-FU), is known as a medicament in the treatment of solid tumors (Seley, K. L. Drugs 4 (1), 99, 2001). The active form, 5,10-$CH_2$-(6R)-THF, achieves its chemotherapeutic effect together with the base analogue and 5-FU metabolite 5-FdUMP by inhibiting the enzyme thymidylate synthase (TS). TS catalyses the conversion of deoxyuridylate (dUMP) to deoxythymidylate (dTMP), which is an essential building block for DNA synthesis. Deactivation of TS occurs by formation of a covalent, ternary inhibition complex between TS, the base analogue 5-FdUMP, which is a metabolite of 5-FU, and 5,10-$CH_2$-(6R)-THF. An enhancement of the cytotoxic effect of 5-FU can be achieved by increasing the intracellular concentration of 5,10-$CH_2$-(6R)-THF, whereupon the stability of the ternary complex is increased. This causes direct inhibition of DNA synthesis and repair, which ultimately results in cell death and delay of tumor growth.

However, there are undesirable properties associated with 5,10-$CH_2$-(6R)-THF that limit its pharmaceutical use. For example, 5,10-$CH_2$-(6R)-THF is highly susceptible to oxidation and chemical degradation that results in unfavorably high impurity levels. Susceptibility to oxidation and chemical degradation of 5,10-$CH_2$-(6R)-THF is especially high when present in its amorphous form and having a large surface e.g. in its pharmaceutical use form as lyophilisate. It is well known that to be amenable for pharmaceutical use the respective composition needs to fulfill several requirements including high chemical and isomeric stability, such that effective storage over an acceptable period of time can be achieved, without exhibiting a significant change in the composition's physicochemical characteristics, ease of handling and processing, etc.

5,10-methylenetetrahydrofolic acid is an addition product of tetrahydrofolic acid and formaldehyde (see e.g. Poe, M. et al. Biochemistry 18 (24), 5527, 1979; Kallen, R. G. Methods in Enzymology 18B, 705, 1971) and is known for its extremely high sensitivity to oxidation by air as well as instability in neutral and/or acidic environments potentially leading to chemical degradation and/or hydrolysis (see e.g. Odin, E. et al., Cancer Investigation 16 (7), 447, 1998; Osborn, M. J. et al., J. Am. Chem. Soc. 82, 4921, 1960; Hawkes, J., and Villota, R. Food Sci. Nutr. 28, 439, 1989). Attempts to stabilize compositions of 5,10-methylenetetrahydrofolates included e.g. (i) rigorous exclusion of atmospheric oxygen by the use of special technical devices for the reconstitution of solid formulations and the injection of 5,10-methylenetetrahydrofolates in an air-free environment (see e.g. Odin, E. et al., Cancer Investigation 16 (7), 447, 1998; U.S. Pat. No. 4,564,054); (ii) addition of a reducing agent such as L(+)-ascorbic acid or salts thereof, reduced gamma-glutathione, beta-mercaptoethanol, thioglycerol, N-acetyl-L-cysteine, etc. as an antioxidant for the highly sensitive 5,10-methylenetetrahydrofolic acid and for tetrahydrofolic acid in particular; (iii) stabilization by means of cyclodextrin inclusion compounds (see e.g. EP 0 579 996); (iv) addition of citrate while adjusting the pH to a basic value (see e.g. EP 1 641 460); or (v) formation of various crystalline forms such as the sulfate salts (see e.g. EP 0 537 492) or hemisulfate salts (see e.g. EP 2 837 631).

There still remains a great need for stable solid state pharmaceutical compositions, especially lyophilisates, of 5,10-$CH_2$-(6R)-THF.

It has now surprisingly been found that certain lyophilisates comprising 5,10-methylene-(6R)-tetrahydrofolic acid [5,10-$CH_2$-(6R)-THF], or a pharmaceutically acceptable salt thereof, and a dicarboxylic acid, or a salt thereof overcomes the previously discussed known drawbacks and allow for the preparation of solid state pharmaceutical compositions of high purity and a low content of either oxidation products or other chemical degradation products. The advantageous stability characteristics of the lyophilisates of the present invention will allow the effective use in medicinal applications.

In the present text, the term pharmaceutically acceptable salts relates to acidic salts, such as sulfate or sulfonate salts, preferably sulfate salts, even more preferably hemisulfate salts, or to alkali or alkaline earth metal salts, preferably sodium, potassium, magnesium or calcium salts.

The addition of a dicarboxylic acid to 5,10-$CH_2$-(6R)-THF helps to maintain the purity of the active ingredient 5,10-$CH_2$-(6R)-THF on a remarkably high level during the lyophilization process and at the same time maintain the amounts of by-products at an acceptable low level. The obtained lyophilized products exhibit a stability over months or more without significant loss of active ingredient, e.g., maintaining the amount of active ingredient at or above 95% and more preferably at or above 98% for several months, including most preferably about 99%, 99.5% or 99.8%. This enables the manufacturing, storage and use of lyophilisates of 5,10-$CH_2$-(6R)-THF without significant decomposition before reconstitution.

It has further been found that lyophilisates of the present invention has a different water content than the corresponding active ingredient.

Lyophilization or freeze-drying is a dehydration process that works by freezing an aqueous solution containing a dissolved material therein and then reducing the surrounding pressure to allow the frozen water to sublime directly from the solid phase to the gas phase. There are usually four stages in a complete lyophilization process: pretreatment, freezing, primary drying, and secondary drying.

Pretreatment includes any method of treating the material prior to freezing. This may include the addition of other components. Pretreatment is possible but not necessary in the preparation of stable lyophilisates comprising 5,10-methylene-(6R)-tetrahydrofolic acid [5,10-$CH_2$-(6R)-THF], or a pharmaceutically acceptable salt thereof, and a dicarboxylic acid, or a salt thereof.

Freezing is often done by placing an aqueous solution of the material in a freeze-drying flask which is cooled by mechanical refrigeration, or using dry ice or liquid nitrogen. On a larger scale, freezing the aqueous solution is usually done using a freeze-drying machine. In this step, it is important to cool the material below its triple point, the lowest temperature at which the solid and liquid phases of the material can coexist. This ensures that sublimation rather than melting will occur in the following steps. Freezing is preferably done at temperatures of −45° C. to −70° C. in the preparation of stable lyophilisates comprising 5,10-methylene-(6R)-tetrahydrofolic acid [5,10-CH$_2$-(6R)-THF], or a pharmaceutically acceptable salt thereof, and a dicarboxylic acid, or a salt thereof.

Annealing for 1 to 2 hours at shelf temperatures around −5° C. to −2° C. is possible but not necessary in the preparation of stable lyophilisates comprising 5,10-methylene-(6R)-tetrahydrofolic acid [5,10-CH$_2$-(6R)-THF], or a pharmaceutically acceptable salt thereof, and a dicarboxylic acid, or a salt thereof.

During the primary drying phase, the pressure is lowered (to the range of a few millibars), and enough heat is supplied to the material for the ice to sublime. In this initial drying phase, about 95% of the water in the material is sublimated. This phase may be slow (can be several days in the industry), because, if too much heat is added, the material's structure could be altered. In the primary drying phase, pressure is controlled through the application of partial vacuum. The vacuum speeds up the sublimation, making it useful as a deliberate drying process. In the preparation of stable lyophilisates comprising 5,10-methylene-(6R)-tetrahydrofolic acid [5,10-CH$_2$-(6R)-THF], or a pharmaceutically acceptable salt thereof, and a dicarboxylic acid, or a salt thereof primary drying phase is started at freezing temperature of preferably of −45° C. to −70° C. Then during primary drying phase temperature is, after an optionally starting period of preferably 10 minutes to 120 minutes at freezing temperature, increased over time to preferably about 0° C. During primary drying phase a pressure of preferably about 50 µbar to 200 µbar is held.

The secondary drying phase aims to remove unfrozen water molecules, since the ice was removed in the primary drying phase. In this phase, the temperature is raised higher than in the primary drying phase, and can even be above 0° C., to break any physico-chemical interactions that have formed between the water molecules and the frozen material. Usually the pressure is also lowered in this stage to encourage desorption (typically in the range of microbars, or fractions of a pascal). Secondary drying is preferably done at temperatures up to about 25° C. to 30° C. and a pressure of about 50 µbar to 200 µbar in the preparation of stable lyophilisates comprising 5,10-methylene-(6R)-tetrahydrofolic acid [5,10-CH$_2$-(6R)-THF], or a pharmaceutically acceptable salt thereof, and a dicarboxylic acid, or a salt thereof.

Primary and secondary drying phase may be combined by having followed a temperature ramp from freezing temperature to temperatures up to about 25° C. to 30° C. and a pressure of about 50 µbar to 200 µbar in the preparation of stable lyophilisates comprising 5,10-methylene-(6R)-tetrahydrofolic acid [5,10-CH$_2$-(6R)-THF], or a pharmaceutically acceptable salt thereof, and a dicarboxylic acid, or a salt thereof. Temperature ramp may contain multiple holding steps where temperature is kept constant for some time. Preferably holding steps, if any, are at freezing temperature, at about 0° C. and at about 25° C. to 30° C.

After the lyophilization process is complete, the vacuum is usually broken with an inert gas, such as nitrogen, before the material is sealed. At the end of the operation, the final residual water content of lyophilisates comprising 5,10-methylene-(6R)-tetrahydrofolic acid [5,10-CH$_2$-(6R)-THF], or a pharmaceutically acceptable salt thereof, and a dicarboxylic acid, or a salt thereof is usually around 1% to 5%.

Stability is a critical property and component of pharmaceutical formulation studies and drug development. Chemical stability studies are performed both in solution and solid state. It is an established fact that solution state and solid state stability can differ both qualitatively and quantitatively. Also in solid state stability of a crystalline material and an amorphous material, such as a lyophilisate can differ. Extensive studies are performed for chemical stability of a drug substance and pharmaceutical compositions thereof by exposing it to variety of stressors, like high temperature and/or high humidity. These studies also provide information on the degradation products and help in developing meaningful specifications as well as the intrinsic stability of the pharmaceutical composition. Most common pathways for drug degradation include i.a. hydrolysis, oxidation, and photochemical degradation.

The purpose of stability testing is to provide evidence on how the quality of a product varies with time under the influence of a variety of environmental factors such as temperature, humidity, and light, and to establish a suitable shelf life for the pharmaceutical product and recommended storage conditions in order to ensure patient safety.

One embodiment is directed to a lyophilisate comprising 5,10-methylene-(6R)-tetrahydrofolic acid [5,10-CH$_2$-(6R)-THF], or a pharmaceutically acceptable salt thereof, and dicarboxylic acid, or a salt thereof.

One embodiment is directed to a lyophilisate comprising 5,10-methylene-(6R)-tetrahydrofolic acid [5,10-CH$_2$-(6R)-THF], or a pharmaceutically acceptable salt thereof, and succinic acid, or a salt thereof.

One embodiment is directed to a lyophilisate comprising 5,10-methylene-(6R)-tetrahydrofolic acid [5,10-CH$_2$-(6R)-THF], or a pharmaceutically acceptable salt thereof, and maleic acid, or a salt thereof.

One embodiment is directed to a lyophilisate comprising 5,10-methylene-(6R)-tetrahydrofolic acid [5,10-CH$_2$-(6R)-THF], or a pharmaceutically acceptable salt thereof, and malic acid, or a salt thereof.

One embodiment is directed to a lyophilisate comprising 5,10-methylene-(6R)-tetrahydrofolic acid [5,10-CH$_2$-(6R)-THF], or a pharmaceutically acceptable salt thereof, and tartaric acid, or a salt thereof.

One embodiment is directed to a lyophilisate comprising 5,10-methylene-(6R)-tetrahydrofolic acid [5,10-CH$_2$-(6R)-THF], or a pharmaceutically acceptable salt thereof, and fumaric acid, or a salt thereof.

One embodiment is directed to a lyophilisate comprising 5,10-methylene-(6R)-tetrahydrofolic acid [5,10-CH$_2$-(6R)-THF], or a pharmaceutically acceptable salt thereof, and oxalic acid, or a salt thereof.

Lyophilisates of the present invention are substantially amorphous while having an enhanced stability, such as an enhanced storage stability.

Lyophilisates of the present invention are further preferably reconstituted into an aqueous pharmaceutical formulation to be administered into a patient in need thereof.

A further aspect is directed to a process for the preparation of the lyophilisates of the present invention which comprises the steps of
  (i) dissolving 5,10-methylene-(6R)-tetrahydrofolic acid, or a pharmaceutically acceptable salt thereof, in water containing a dicarboxylic acid, or a salt thereof;
  (ii) freezing the water; and
  (iii) thereafter removing the frozen water under vacuum.

Optionally an aqueous base, like NaOH or KOH is added in step (i) to complete dissolution of the 5,10-methylene-(6R)-tetrahydrofolic acid compound.

The solution of step a can optionally be filtered through a sterile filter, before step (ii) is performed.

The pH of the solution in step (i) is above 6, usually about 8-14, preferably about 9.3.

A further aspect is directed to reconstituted pharmaceutical compositions of the lyophilisates of the present invention comprising a 5,10-methylene-(6R)-tetrahydrofolic acid [5,10-CH$_2$-(6R)-THF], or a pharmaceutically acceptable salt thereof, and a dicarboxylic acid, or a salt thereof and a pharmaceutically acceptable carrier or diluent, such as sterile water or a liquid pharmaceutically acceptable vehicle, optionally further comprising at least one additional therapeutic agent including but not limited to, bactericides, antibiotics, antivirals, antiseptics, antineoplastics, anticancer compounds such as chemotherapeutic agents, antifungals, and/or anti-inflammatory agents or other bioactive or therapeutic agents that are suitable for human use, in particular anticancer compounds such as chemotherapeutic agents, for example 5-FU and derivatives, and antifolates, e.g. methotrexate, Pemetrexed.

"Liquid pharmaceutically acceptable vehicle" refers to propylene glycol, a polyethylene glycol, ethanol, dimethyl sulfoxide (DMSO), N-methylpyrrolidinone (NMP), glycofurol, isopropylidene glycerol (Solketal), glycerol formal, acetone, tetrahydrofurfuryl alcohol, monoglyme, diglyme, dimethyl isosorbide or ethyl lactate, mixtures thereof, or aqueous mixtures thereof.

A further aspect is directed to the use the reconstituted pharmaceutical compositions of the present invention in therapy, preferably in cancer chemotherapy.

Optionally, the reconstituted pharmaceutical compositions of the present invention may further comprise at least one additional therapeutic agent. In specific embodiments the at least one additional therapeutic agent may be selected from bactericides, antibiotics, antivirals, antiseptics, antineoplastics, anticancer compounds such as chemotherapeutic agents, antifungals, and/or anti-inflammatory agents or other bioactive or therapeutic agents that are suitable for human use, in particular anticancer compounds such as chemotherapeutic agents. An anticancer drug such as a chemotherapeutic agent, may include but is not limited to chemotherapeutic agents that comprise specific binding members, proteins, nucleic acids or nucleic acid analogs (such as, but not limited to antisense molecules, ribozymes, and siRNAs), lipids, steroids, large molecules, small molecules, or metals. The one or more anticancer drugs can comprise one or more chemotherapeutic agents, such as but not limited to: nucleic acids, in particular fluorinated nucleic acids (e.g. 5-flurouracil or an analog or prodrug thereof), antifolates (e.g. pemetrexed, raltitrexed, lometrexol), topoisomerase inhibitors (e.g. irinotecan, topotecan), antimetabolite drugs (e.g. methotrexate, gemcitabine, tezacitabine), 5-FU modulators, alkylating agents (e.g. cyclophosphamide, carmustine), nucleic acid biosynthesis inhibitors (such as mitomycin, anthracyclines (e.g. epirubicin, doxorubicin), platinum derivatives (e.g. cisplatin, oxaliplatin, carboplatin), microtubule disrupting drugs (e.g. paclitaxel, docetaxel, vinolrebine, vincristine), hormone blocking drugs (e.g. tamoxifen), inhibitors of kinases, including but not limited to receptor and nonreceptor tyrosine kinases (e.g. Iressa, Tarceva, SU5416, PTK787, Gleevec), proteosome inhibitors (e.g. bortezomib), immune modulators (e.g. levamisole), anti-inflammatory drugs, vascularization inhibitors, cytokines (e.g. interleukins, tumor necrosis factors), and drugs that inhibit the activity of cytokines, hormones, or receptors for cytokines or hormones (e.g. the anti-VEGF antibody bevacizumab or "Avastin"). Anticancer drugs may also include monoclonal antibodies, such as but not limited to monoclonal antibodies that bind cytokines, hormones, or hormone receptors (e.g. antibodies that block activation of EGF or VEGF growth factors, such as Avastin, Erbitux, herceptin), etc.

In further aspects, the reconstituted pharmaceutical compositions of the present invention are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors.

Additionally, the reconstituted pharmaceutical compositions of the present invention are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4 [7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9 cis-retinoic acid, α-difluoromethylornithine, ILX23-7553, trans-N-(4'-hydroxyphenyl)retinamide and N 4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)-mu-[diamineplatinum(II)]bis[diamine(chloro)platinum(II)] tetrachloride, diarisidinylspermine, arsenic trioxide, 1 (11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13 deoxo-10-hydroxycarminomycin, annamycin, galarubicin, elinafide, MEN10755 and 4 demethoxy-3 deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro- 4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Topoisomerase inhibitors are, for example, topotecan, hycaptamine, irinotecan, rubitecan, 6 ethoxypropionyl-3',4'-O-exobenzylidenechartreusin, 9 methoxy-N,N-dimethyl-5-nitropyrazolo[3,4,5-kl]acridine-2-(6H)propanamine, 1-amino-9-ethyl-5-fluoro-2,3 dihydro-9-hydroxy-4-methyl-1H,12H-benzo[de]pyrano[3',4':b,7]indolizino[1,2b]quinoline-10,13(9H,15H)-dione, lurtotecan, 7 [2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N [2-(dimethylamino)ethyl]-9-hydroxy-5,6-dimethyl-6H-pyrido[4,3-b]carbazole-1-carboxamide, asulacrine, (5a,5aB,8aa, 9b)-9-[2-[N-[2-(dimethylamino)ethyl]-N-methylamino]ethyl]-5-[4-hydroxy-3,5-dimethoxyphenyl]-5,5a,6,8,8a,9 hexohydrofuro(3',4':6,7)naphtho(2,3 d)-1,3 dioxol-6-one, 2,3-(methylene-dioxy)-5-methyl-7-hydroxy-8-methoxy-benzo[c]phenanthridinium, 6,9-bis[(2-aminoethyl)-amino]benzo[g]isoquinoline-5,10-dione, 5 (3-aminopropylamino)-7,10-dihydroxy-2-(2-hydroxyethylaminomethyl)-6H-pyrazolo[4,5,1-de]acridin-6-one, N-[1-[2(diethylamino)-ethylamino]-7-methoxy-9-oxo-9H-thioxanthen-4-ylmethyl] formamide, N-(2-(dimethyl-amino)ethyl)acridine-4-carboxamide, 6-[[2-(dimethylamino)ethyl]amino]-3-hydroxy-7H-indeno[2,1 c]quinolin-7-one and dimesna.

"Antiproliferative agents" include antisense RNA and DNA oligonucleotides such as G3139, ODN698, RVASK-RAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N [5-(2,3-dihydrobenzofuryl)-sulfonyl]-N'-(3,4-dichlorophenyl)urea, N6-[4-deoxy-4-[N2-[2(E),4(E)-tetradecadienoyl]-glycylamino]-L-glycero-β-L-mannoheptopyranosyl]adenine, aplidine, ecteinascidin, troxacitabine, 4 [2-amino-4-oxo-4,6,7,8-tetrahydro-3H-pyrimidino[5,4-b]-1,4-thiazin-6-yl-(S)-ethyl]-2, 5-thienoyl-L-glutamic acid, aminopterin, 5 fluorouracil, alanosine, 11-acetyl-8-(carbamoyloxymethyl)-4-formyl-6-methoxy-14-oxa-1,11-diazatetracyclo(7.4.1.0.0)tetradeca-2, 4,6-trien-9-ylacetic acid ester, swainsonine, lometrexol, dexrazoxane, methioninase, 2'-cyano-2'-deoxy-N4-palmitoyl-1-β-D-arabinofuranosyl cytosine and 3 aminopyridine-2 carboxaldehyde thiosemicarbazone.

"Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

The medicaments of the following table are preferably, but not exclusively, combined with the reconstituted pharmaceutical compositions of the present invention.

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | BBR-3464 (Hoffrnann-La Roche) |
| | Ormiplatin | SM-11355 (Sumitomo) |
| | Iproplatin | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma- Tau) |
| | Irinotecan (CPT-11) | Diflomotecan (Beaufour-Ipsen) |
| | 7-Ethyl-10-hydroxycamptothec: | |
| | Topotecan | TAS-103 (Taiho) |
| | Dexrazoxanet (TopoTarget) | Elsamitrucin (Spectrum) |
| | Pixantrone (Novuspharrna) | J-107088 (Merck & Co) |
| | Rebeccamycin analogue (Exelixis) | BNP-1350 (BioNumerik) |
| | | CKD-602 (Chong Kun Dang) |
| | BBR-3576 (Novuspharrna) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |

| | -continued | |
|---|---|---|
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxorubicin | GPX-100 (Gem Pharmaceuticals) |
| | Mitoxantron (Novantron) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCI) | D 24851 (ASTA Medica) |
| | Rhizoxin (Fujisawa) | ER-86526 (Eisai) |
| | Mivobulin (Warner-Lambert) | Combretastatin A4 (BMS) |
| | Cemadotin (BASF) | Isohomohalichondrin-B |
| | RPR 109881A (Aventis) | (PharmaMar) |
| | TXD 258 (Aventis) | ZD 6126 (AstraZeneca) |
| | Epothilone B (Novartis) | PEG-Paclitaxel (Enzon) |
| | T 900607 (Tularik) | AZ10992 (Asahi) |
| | T 138067 (Tularik) | !DN-5109 (Indena) |
| | Cryptophycin 52 (Eli Lilly) | AVLB (Prescient NeuroPharma) |
| | Vinflunine (Fabre) | Azaepothilon B (BMS) |
| | Auristatin PE (Teikoku Hormone) | BNP- 7787 (BioNumerik) |
| | BMS 247550 (BMS) | CA-4-prodrug (OXiGENE) |
| | BMS 184476 (BMS) | Dolastatin-10 (NrH) |
| | BMS 188797 (BMS) | CA-4 (OXiGENE) |
| | Taxoprexin (Protarga) | |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | lonafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyltransferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT -3 (CollaGenex) |
| | Marimastat (British Biotech) | BMS-275291 (Celltech) |
| Ribonucleoside reductase inhibitors | Gallium maltolate (Titan) | Tezacitabine (Aventis) |
| | Triapin (Vion) | Didox (Molecules for Health) |
| TNF-alpha agonists/ antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | Pentrix (Australian Cancer Technology) |
| | GMK (Progenics) | |
| | Adenocarcinoma vaccine (Biomira) | JSF-154 (Tragen) |
| | CTP-37 (AVI BioPharma) | Cancer vaccine (Intercell) |
| | JRX-2 (Immuno-Rx) | Norelin (Biostar) |
| | PEP-005 (Peplin Biotech) | BLP-25 (Biomira) |
| | Synchrovax vaccines (CTL Immuno) | MGV (Progenies) |
| | Melanoma vaccine (CTL Immuno) | !3-Alethin (Dovetail) |
| | p21-RAS vaccine (GemVax) | CLL-Thera (Vasogen) |
| Hormonal and antihormonal agents | Oestrogens | Prednisone |
| | Conjugated oestrogens | Methylprednisolone |
| | Ethynyloestradiol | Prednisolone |
| | chlorotrianisene | Aminoglutethimide |

-continued

|  | Idenestrol | Leuprolide |
|---|---|---|
|  | Hydroxyprogesterone caproate | Goserelin |
|  | Medroxyprogesterone | Leuporelin |
|  | Testosterone | Bicalutamide |
|  | Testosterone propionate | Flutamide |
|  | Fluoxymesterone | Octreotide |
|  | Methyltestosterone | Nilutamide |
|  | Diethylstilbestrol | Mitotan |
|  | Megestrol | P-04 (Novogen) |
|  | Tamoxifen | 2-Methoxyoestradiol (EntreMed) |
|  | Toremofin | Arzoxifen (Eli Lilly) |
|  | Dexamethasone |  |
| Photodynamic agents | Talaporfin (Light Sciences) | Pd-bacteriopheophorbide (Yeda) |
|  | Theralux (Theratechnologies) | Lutetium-Texaphyrin (Pharmacyclics) |
|  | Motexafin-Gadolinium (Pharmacyclics) | Hypericin |
| Tyrosine kinase inhibitors | Imatinib (Novartis) | Kahalide F (PharmaMar) |
|  | Leflunomide (Sugen/Pharmacia) | CEP- 701 (Cephalon) |
|  | ZD1839 (AstraZeneca) | CEP-751 (Cephalon) |
|  | Erlotinib (Oncogene Science) | MLN518 (Millenium) |
|  | Canertjnib (Pfizer) | PKC412 (Novartis) |
|  | Squalamine (Genaera) | Phenoxodiol O |
|  | SU5416 (Pharmacia) | Trastuzumab (Genentech) |
|  | SU6668 (Pharmacia) | C225 (ImClone) |
|  | ZD4190 (AstraZeneca) | rhu-Mab (Genentech) |
|  | ZD6474 (AstraZeneca) | MDX-H210 (Medarex) |
|  | Vatalanib (Novartis) | 2C4 (Genentech) |
|  | PKI166 (Novartis) | MDX-447 (Medarex) |
|  | GW2016 (GlaxoSmithKline) | ABX-EGF (Abgenix) |
|  | EKB-509 (Wyeth) | IMC-1C11 (ImClone) |
|  | EKB-5 69 (Wyeth) |  |
| Various agents | SR-27 897 (CCK-A inhibitor, Sanofi-Synthelabo) | BCX-1777 (PNP inhibitor, BioCryst) |
|  | Tocladesine (cyclic AMP agonist, Ribapharm) | Ranpirnase (ribonuclease stimulant, Alfacell) |
|  | Alvocidib (CDK inhibitor, Aventis) | Galarubicin (RNA synthesis inhibitor, Dong-A) |
|  | CV-247 (COX-2 inhibitor, Ivy Medical) | Tirapazamine (reducing agent, SRI International) |
|  | P54 (COX-2 inhibitor, Phytopharm) | N-Acetylcysteine (reducing agent, Zambon) |
|  | CapCell ™ (CYP450 stimulant, Bavarian Nordic) | R-Flurbiprofen (NF-kappaB inhibitor, Encore) |
|  | GCS-IOO (gal3 antagonist, GlycoGenesys) | 3CPA (NF-kappaB inhibitor, Active Biotech) |
|  | G17DT immunogen (gastrin inhibitor, Aphton) | Seocalcitol (vitamin D receptor agonist, Leo) |
|  | Efaproxiral (oxygenator, AlIos Therapeutics) | 131-I-TM-601 (DNA antagonist, TransMolecular) |
|  | PI-88 (heparanase inhibitor, Progen) | Eflornithin (ODC inhibitor, ILEX Oncology) |
|  | Tesmilifen (histamine antagonist, YM BioSciences) | Minodronic acid (osteoclast inhibitor, Yamanouchi) |
|  | Histamine (histamine H2 receptor agonist, Maxim) | Indisulam (p53 stimulant, Eisai) |
|  | Tiazofurin (IMPDH inhibitor, Ribapharm) | Aplidine (PPT inhibitor, PharmaMar) |
|  | Cilengitide (integrin antagonist, Merck KGaA) | Rituximab (CD20 antibody, Genentech) |
|  | SR-31747 (IL-1 antagonist, Sanofi-Synthelabo) | Gemtuzumab (CD33 antibody, Wyeth Ayerst) |
|  | CCI-779 (mTOR kinase inhibitor, Wyeth) | PG2 (haematopoiesis promoter, Pharmagenesis) |
|  | Exisulind (PDE-V inhibitor, Cell Pathways) | Immunol ™ (triclosan mouthwash, Endo) |
|  | CP-461 (PDE-V inhibitor, Cell Pathways) | Triacetyluridine (uridine prodrug, Wellstat) |
|  | AG-2037 (GART inhibitor, Pfizer) | SN-4071 (sarcoma agent, Signature BioScience) |
|  | WX-UK1 (plasminogen activator inhibitor, Wilex) | TransMID-107 ™ (immunotoxin, KS Biomedix) |
|  | PBI-1402 (PMN stimulant, ProMetic LifeSciences) | PCK-3145 (apoptosis promoter, Procyon) |
|  | Bortezomib (proteasome inhibitor, Millennium) | Doranidazole (apoptosis promoter, Pola) |
|  | SRL-172 (T-cell stimulant, SR Pharma) | CHS-828 (cytotoxic agent, Leo) |
|  | TLK-286 (glutathione-S transferase inhibitor, Telik) | trans-Retinic acid (differentiator, NIH) |

| | |
|---|---|
| PT-100 (growth factor agonist, Point Therapeutics) | MX6 (apoptosis promoter, MAXIA) |
| Midostaurin (PKC inhibitor, Novartis) | Apomine (apoptosis promoter, ILEX Oncology) |
| Bryostatin-1 (PKC stimulant, GPC Biotech) | Urocidine (apoptosis promoter, Bioniche) |
| CDA-II (apoptosis promoter, Everlife) | Ro-31-7453 (apoptosis promoter, La Roche) |
| SDX-101 (apoptosis promoter, Salmedix) | Brostallicin (apoptosis promoter, Pharmacia) |
| Ceflatonin (apoptosis promoter, ChemGenex) | |

The reconstituted pharmaceutical compositions of the present invention may be used for therapy, specifically in cancer chemotherapy, i.e. in a method for treatment of cancer, which comprises administering a therapeutically effective amount of 5,10-$CH_2$-(6R)-THF to a subject in need of such treatment.

In another embodiment, reconstituted pharmaceutical compositions of the present invention is used in therapy, preferably in chemotherapy, i.e. in the treatment of cancer. Examples of cancers to be treated include, but are not limited to, breast cancer, esophageal cancer, gastric cancer, gall bladder cancer, bile duct cancer, colon cancer, rectal cancer, liver cancer, pancreatic cancer, ovarian cancer, head and neck cancer, and mesotheolioma cancer.

In a preferred embodiment the cancer is selected from various cancer forms including colon cancer, stomach cancer, breast cancer, bowel cancer, gallbladder cancer, lung cancer (specifically adenocarcinoma), colorectal cancer (CRC) including metastatic CRC, head and neck cancer, liver cancer and pancreatic cancer.

The reconstituted pharmaceutical compositions of the present invention are in a form suitable for parenteral administration, such as intravenously or intramuscularly, subcutaneously, intra-arterially.

For parenteral administration, fluid unit dosage forms typically comprise reconstituted lyophilisates, preferably reconstituted pharmaceutical compositions of the present invention, optionally a further therapeutic agent, and a pharmaceutically acceptable carrier or diluent, to form e.g. water-based solutions or oil-based suspensions. For parenteral solutions, the lyophilisates of the present invention may be filter sterilized during its preparation, e.g. before filling into a suitable vial or ampoule.

In case of a combination therapy of reconstituted pharmaceutical composition of the present invention and at least one further therapeutic agent, the active agents may be administered as part of the same pharmaceutical composition or the at least one further therapeutic agent may be administered separately, i.e. as a separate (and possibly different) pharmaceutical compositions, optionally via different administration routes, either simultaneously or sequentially.

The dose of the active agent(s), i.e. 5,10-$CH_2$-(6R)-THF (and optionally the at least one further therapeutic agent), used in a treatment as described herein, will depend on various factors, including age and health condition of the subject to be treated, type and severity of the disease to be treated, and frequency of administration, and the like. Those skilled in the art of cancer treatment and chemotherapy would be able to determine therapeutically effective amounts and regimens for the active pharmaceutical ingredient 5,10-$CH_2$-(6R)-THF alone or in combination with at least one further therapeutic agent as defined above, based on known protocols for evaluating toxicity and efficacy.

The term "therapeutically effective amount" refers to the amount of active compound that elicits the biological or medicinal response in a tissue, system, animal, individual or human that is being sought by a skilled practitioner (e.g. researcher, veterinarian, medical doctor or other clinician or caregiver), which includes (i) prevention of the disease; and/or (ii) inhibition of the disease (e.g. arresting further development of the pathology and/or symptomatology); and/or (iii) amelioration of the disease (e.g. reversing the pathology and/or symptomatology). Likewise, the term "treatment" as used herein refers to (i) prevention of the disease; and/or (ii) inhibition of the disease (e.g. arresting further development of the pathology and/or symptomatology); and/or (iii) amelioration of the disease (e.g. reversing the pathology and/or symptomatology).

A pharmaceutical composition of choice may contain from 0.1% to 99 wt %, preferably from 10 to 60 wt %, of the active pharmaceutical ingredient (i.e. 5,10-$CH_2$-(6R)-THF optionally in combination with at least one further therapeutic agent), depending on the method of administration.

Typical dosage ranges of the 5,10-$CH_2$-(6R)-THF to be used in cancer treatment may range from 5 $mg/m^2$ to 1.5 $g/m^2$, preferably from 30 $mg/m^2$ to 500 $mg/m^2$ (for colorectal cancer treatment) resp. 10 $mg/m^2$ to 1000 $mg/m^2$ (for Methotrexate therapy), and more preferably from about 60 $mg/m^2$ to about 300 $mg/m^2$ (for colorectal cancer treatment) resp. 50 $mg/m^2$ to 500 $mg/m^2$ (for Methotrexate therapy).

The terms "isomeric purity" resp. "stereoisomeric purity", as used herein, refer to the amount of 5,10-$CH_2$-(6R)-THF in a sample, which may contain one or more other isomers of the same compound. The terms "isomerically pure" resp. "stereoisomerically pure", as used herein, mean 5,10-$CH_2$-(6R)-THF in isomeric excess over other isomers greater than about 80%, preferably greater than about 90%, preferably greater than about 95%, more preferably greater than about 97%, even more preferably greater than about 99%, more preferably greater than about 99.5% or more, and most preferably up to 100%, wherein the remainder may be one or more of the other isomers.

The term "chemical purity," as used herein, means percentage of a particular compound in a sample. The term "substantial chemical purity", as used herein, refers to a compound in about 80% chemical purity, preferably about 90%, more preferably about 95%, more preferably about 97%, more preferably about 98% chemical purity, and most preferably 99% or higher than 99%, e.g., 99.5, 99.6, 99.7, 99.8, 99.9 or up to 100% chemical purity, as determined by HPLC. Chemical impurities may include unreacted starting material (including solvents), degradation products of 5,10-$CH_2$-(6R)-THF (such as tetrahydrofolic acid and its degradation products), etc.

The term "pharmaceutically acceptable" as used herein indicates that the carrier is approved or recognized for use in animals, and more particularly in humans, i.e. it is not toxic to the host or patient. In addition, a carrier of choice will not interfere with the effectiveness of the biological activity of the active ingredient. The term "carrier" refers to any auxiliary material necessary for the particular mode of administration of choice and includes e.g. solvents (diluents) excipients, or other additives with which the lyophilisates of the present invention is administered. Typically used diluents pharmaceutical carriers include sterile liquids, such as aqueous solutions and oils (e.g. of petroleum, animal, vegetable or synthetic origin), e.g. peanut oil, soybean oil, mineral oil, sesame oil and the like. Typically used aqueous liquids include water, saline solutions, aqueous dextrose and glycerol solutions and the like. Suitable pharmaceutical excipients include starch, glucose, lactose, sucrose, gelatine, malt, rice, flour, chalk, silica gel, sodium stearate, glycerol monostearate, talc, dried skim milk, glycerol, propylene, glycol, water, ethanol and the like. Examples of suitable pharmaceutical carriers are well known in the art and are described in e.g. "Remington's Pharmaceutical Sciences" by E. W. Martin (18th ed., Mack Publishing Co., Easton, Pa. (1990).

EXAMPLES

Exemplary Process Parameters of the Lyophilization.

| Step | | Shelf temperature | Ice condenser temperature | Pressure | Time step | Cumulative time |
|---|---|---|---|---|---|---|
| 1 | Loading | 4 | — | atm | 00:01 | 0:01 |
| 2 | Freezing, ramp | −45 | — | atm | 01:30 | 1:31 |
| 3 | Freezing | −45 | — | atm | 02:00 | 3:31 |
| 4 | Vacuum adjustment | −45 | −70 | 0.05 | 00:30 | 4:01 |
| 5 | Primary drying, ramp | 0 | −70 | 0.05 | 01:45 | 5:46 |
| 6 | Primary drying | 0 | −70 | 0.05 | 41:00 | 46:46 |
| 7 | Secondary drying, ramp | 25 | −70 | 0.05 | 12:00 | 58:46 |
| 8 | Secondary drying | 25 | −70 | 0.05 | 06:00 | 64:46 |

Online data recorded during a lyophilization is shown in FIG. 1.

Example 1: Lyophilisate Containing 5,10-methylen-(6R)-tetrahydrofolic Acid and Malic Acid Under nitrogen 210 g purified water and 16.5 g sodium hydroxide 2M were cooled down to 3±2° C. (resulting pH 14.0). 6.96 g malic acid and then 5.70 g 5,10-methylene-(6R)-tetrahydrofolic acid hemisulfate salt were added (pH is decreasing to 13.0) and rinsed with 2.5 g purified water. By the addition of sodium hydroxide 2M pH is held at 9.3±0.1. 11.65 g purified water were added. Overall 2.15 g sodium hydroxide 2M pH were needed to keep the pH at 9.3±0.1.

5.0 ml of the resulting clear solution (being 5.181 g to 5.184 g) were introduced per vial into 10 ml glass vials (36 vials). Vials were immediately frozen with liquid nitrogen and lyophilised at <10⁻¹ mbar.

Vials obtained were containing a lyophilisate of 102 mg 5,10-methylene-(6R)-tetrahydrofolic acid (calculated as free acid) with malic acid. Cake weight was 258 mg. 5,10-methylene-(6R)-tetrahydrofolic acid is showing a purity of 97.42% area measured by HPLC. Water content was 2.7% w/w resp. 7.0 mg per vial.

When reconstituted solution is having an osmolality of 253 mosmol/kg.

Example 2: Lyophilisate Containing 5,10-methylen-(6R)-tetrahydrofolic Acid and Succinic Acid Under nitrogen 210 g purified water and 16.5 g sodium hydroxide 2M were cooled down to 3±2° C. (resulting pH 14.0). 10.56 g sodium succinate hexahydrate and then 5.70 g 5,10-methylene-(6R)-tetrahydrofolic acid hemisulfate salt were added (pH is decreasing to 13.8) and rinsed with 2.5 g purified water. By the addition of sodium hydroxide 2M pH is held at 9.3±0.1. 12.74 g purified water were added. Overall 14.8 g sodium hydroxide 2M pH were needed to keep the pH at 9.3±0.1.

5.0 ml of the resulting clear solution (being 5.0959 g and 5.1079 g) were introduced per vial into 10 ml glass vials (36 vials). Vials were immediately frozen with liquid nitrogen and lyophilised at <10⁻¹ mbar.

Vials obtained were containing a lyophilisate of 102 mg 5,10-methylene-(6R)-tetrahydrofolic acid (calculated as free acid) with succinic acid. Cake weight was 242 mg. 5,10-methylene-(6R)-tetrahydrofolic acid is showing a purity of 97.35% area measured by HPLC. Water content was 1.1% w/w resp. 2.6 mg per vial.

When reconstituted solution is having an osmolality of 267 mosmol/kg.

Example 3: Lyophilisate Containing 5,10-methylen-(6R)-tetrahydrofolic Acid and Maleic Acid Under nitrogen 210 g purified water and 16.5 g sodium hydroxide 2M were cooled down to 3±2° C. 13.92 g di-sodium maleate hydrate and then 5.70 g 5,10-methylene-(6R)-tetrahydrofolic acid hemisulfate salt were added (pH is decreasing to 13.8) and rinsed with 2.5 g purified water. Cooling was withdrawn and temperature was let to increase to room temperature.

By the addition of sodium hydroxide 2M pH is held at 9.3±0.1. 17.05 g purified water were added. Overall 18.4 g sodium hydroxide 2M pH were needed to keep the pH at 9.3±0.1. The clear solution was kept for 2 hours at room temperature.

5.0 ml of the resulting clear solution were introduced per vial into 10 ml glass vials (7 vials). Vials were lyophilised.

Vials obtained were containing a lyophilisate of 5,10-methylene-(6R)-tetrahydrofolic acid with maleic acid. 5,10-methylene-(6R)-tetrahydrofolic acid is showing a purity of 97.54% area measured by HPLC.

Example 4: Lyophilisate Containing 5,10-methylen-(6R)-tetrahydrofolic Acid and Fumaric Acid Under nitrogen 210 g purified water and 16.5 g sodium hydroxide 2M were cooled down to 3±2° C. 6.26 g di-sodium fumarate and then 5.70 g 5,10-methylene-(6R)-tetrahydrofolic acid hemisulfate salt were added (pH is decreasing to 13.8) and rinsed with 2.5 g purified water. Cooling was withdrawn and temperature was let to increase to room temperature.

By the addition of sodium hydroxide 2M pH is held at 9.3±0.1. 17.66 g purified water were added. Overall 19.1 g sodium hydroxide 2M pH were needed to keep the pH at 9.3±0.1. The clear solution was kept for 2 hours under argon at room temperature.

5.0 ml of the resulting clear solution were introduced per vial into 10 ml glass vials (7 vials). Vials were lyophilised.

Vials obtained were containing a lyophilisate of 5,10-methylene-(6R)-tetrahydrofolic acid with fumaric acid. 5,10-methylene-(6R)-tetrahydrofolic acid is showing a purity of 96.80% area measured by HPLC.

Example 5: Long Term Stability of Lyophilisates Containing 5,10-methylen-(6R)-tetrahydrofolic acid and a dicarboxylic acid (Content of (6R)-5,10-CH$_2$-THF)

In order to determine the long-term stabilities of lyophilisates of 5,10-CH$_2$-(6R)-THF prepared according to Examples 1-4, lyophilisates were stored in air at +5° C., +25° C./60% relative humidity and +40° C./75% relative humidity. The content of 5,10-CH$_2$-(6R)-THF remaining was measured by HPLC at periodic intervals and is given by comparison with the initial value (% rel.). The results are shown in Tables 1 and 2.

TABLE 1

Long-term stability of a lyophilisate containing 5,10-methylen-(6R)-tetrahydrofolic acid and malic acid

| | Relative content of (6R)-5,10-CH$_2$-THF over storage time [months] | | | | | |
|---|---|---|---|---|---|---|
| | 0 | 1 | 2 | 3 | 6 | 12 |
| +5° C. | 100.0 | | 101.2 | 100.1 | 100.0 | 101.5 |
| +25° C./60% rh | 100.0 | 99.3 | 101.0 | 99.8 | 98.6 | 100.9 |
| +40° C./75% rh | 100.0 | 99.5 | 100.6 | 100.1 | 99.4 | |

TABLE 2

Long-term stability of a lyophilisate containing 5,10-methylen-(6R)-tetrahydrofolic acid and succinic acid

| | Relative content of (6R)-5,10-CH$_2$-THF over storage time [months] | | | | | |
|---|---|---|---|---|---|---|
| | 0 | 1 | 2 | 3 | 6 | 12 |
| +5° C. | 100.0 | | 98.8 | 99.0 | (75.8)[1] | 100.5 |
| +25° C./60% rh | 100.0 | 98.0 | 99.4 | 98.8 | 98.9 | 98.8 |
| +40° C./75% rh | 100.0 | 98.1 | 98.7 | 98.4 | 96.7 | |

[1]Most likely lab error

Tables 1 and 2 clearly show that lyophilsates of 5,10-CH$_2$-(6R)-THF are highly stable over a long period of time even at elevated temperatures.

Example 6: Long Term Stability of Lyophilisates Containing 5,10-methylen-(6R)-tetrahydrofolic Acid and a Dicarboxylic Acid (Content of Stability Indicator 10-formyl-(6R)-tetrahydrofolic Acid)

In order to determine the long-term stabilities of lyophilisates of (6R)-5,10-CH$_2$-THF prepared according to Examples 1-4, lyophilisates were stored in air at +5° C., +25° C./60% relative humidity and +40° C./75% relative humidity. The content of the main degradation product 10-formyl-(6R)-tetrahydrofolic acid was measured by HPLC at periodic intervals. The results are shown in Tables 3 and 4.

TABLE 3

Long-term stability of a lyophilisate containing 5,10-methylen-(6R)-tetrahydrofolic acid and malic acid

| | Content of 10-formyl-(6R)-tetrahydrofolic acid over storage time [months] | | | | | |
|---|---|---|---|---|---|---|
| | 0 | 1 | 2 | 3 | 6 | 12 |
| +5° C. | 0.16 | | 0.18 | 0.18 | 0.16 | 0.17 |
| +25° C./60% rh | 0.16 | 0.18 | 0.18 | 0.19 | 0.17 | 0.17 |
| +40° C./75% rh | 0.16 | 0.18 | 0.18 | 0.19 | 0.18 | |

TABLE 4

Long-term stability of a lyophilisate containing 5,10-methylen-(6R)-tetrahydrofolic acid and succinic acid

| | Content of 10-formyl-(6R)-tetrahydrofolic acid over storage time [months] | | | | | |
|---|---|---|---|---|---|---|
| | 0 | 1 | 2 | 3 | 6 | 12 |
| +5° C. | 0.14 | | 0.15 | 0.17 | 0.15 | 0.15 |
| +25° C./60% rh | 0.14 | 0.17 | 0.17 | 0.19 | 0.18 | 0.20 |
| +40° C./75% rh | 0.14 | 0.19 | 0.21 | 0.22 | 0.22 | |

Tables 3 and 4 confirm that lyophilsates of 5,10-CH$_2$-(6R)-THF are highly stable over a long period of time even at elevated temperatures.

No melting or collapse occurs during the lyophilization process of 5,10-CH$_2$-(6R)-THF according to the present invention. Process is running at shelf temperature of 30° C. and pressure of 200 μbar.

Extensive cake shrinkage is reduced, but a lid showing a dense structure is formed on top of the lyophilisates of the present invention. Optionally, annealing for 1 to 2 hours at temperatures around −5° C. to −2° C. is performed.

Example 7: Stability of Reconstituted Lyophilisates Containing 5,10-methylen-(6R)-tetrahydrofolic Acid and a Dicarboxylic Acid In order to determine the stabilities of reconstituted lyophilisates of (6R)-5,10-CH$_2$-THF prepared according to Examples 1-4, lyophilisates containing 5,10-methylen-(6R)-tetrahydrofolic acid per vial were re-dissolved in 10 mL water (dissolving time). After further 50 min the content of 5,10-methylen-(6R)-tetrahydrofolic acid was measured. Then the solution was cooled to −18° C. and stored for 12 days at −18° C. After that the content of 5,10-methylen-(6R)-tetrahydrofolic acid was again measured. The vials were then warmed up to room temperature and stored for another 5 days. Then the content of 5,10-methylen-(6R)-tetrahydrofolic acid was again measured. Corresponding reference vials containing 5,10-methylen-(6R)-tetrahydrofolic acid and tri-sodium citrate, 5,10-methylen-(6R)-tetrahydrofolic acid and sodium acetate, and just 5,10-methylen-(6R)-tetrahydrofolic acid (without a dicarboxylic acid) were treated and measured equivalently. All results (measured by HPLC) were calculated relative to the initial value. The results are shown in Table 5.

TABLE 5

Stability of reconstituted lyophilsates containing 5,10-methylen-(6R)-tetrahydrofolic acid and a dicarboxylic acid

| | | Content of 10-formyl-(6R)-tetrahydrofolic acid over storage time after | | | |
|---|---|---|---|---|---|
| 5,10-methylen-(6R)-tetrahydrofolic acid and . . . | Dissolving time [min] | 0-value room temperature | further 50 min at room temperature | further 12 days at −18° C. | further 5 days at room temperature |
| tri-sodium citrate (Reference) | 55 | 100.0 | 99.52 | 99.10 | 74.75 |
| di-sodium fumarate | 74 | 100.0 | 99.42 | 97.54 | 68.39 |
| di-sodium maleate | 69 | 100.0 | 99.53 | 97.80 | 70.75 |
| sodium acetate (Reference) | 73 | 100.0 | 99.46 | 97.68 | 65.92 |
| - (Reference) | 66 | 100.0 | 99.26 | 98.70 | 63.48 |

Table 5 confirms that reconstituted lyophilsates of 5,10-CH$_2$-(6R)-THF are acceptably stable over time when stored at low temperatures.

BRIEF DESCRIPTION OF THE DRAWING

FIG. 1 shows data recorded for an example of the lyophilization method.

The invention claimed is:

1. A stable lyophilisate comprising 5,10-methylen-(6R)-tetrahydrofolic acid, or a pharmaceutically acceptable salt thereof, and a dicarboxylic acid, or a salt thereof.

2. A stable lyophilisate according to claim 1, wherein the dicarboxylic acid is succinic, maleic, malic, tartaric, fumaric or oxalic acid.

3. A stable lyophilisate according to claim 1, having a chemical purity of greater than 98% and a stereoisomeric purity of greater than 99%.

4. A reconstituted product obtained by dissolving the lyophilisate of claim 1 in water or a liquid pharmaceutically acceptable vehicle.

5. A reconstituted product according to claim 4, wherein the water is sterile water for injection.

6. A reconstituted product according to claim 4, further comprising a pharmaceutically acceptable carrier.

7. A reconstituted product according to claim 4, further comprising an additional pharmaceutically acceptable active ingredient.

8. A reconstituted product according to claim 4, further comprising a buffer.

9. A process for preparing a lyophilisate according to claim 1 comprising the steps of
   (i) dissolving 5,10-methylene-(6R)-tetrahydrofolic acid, or a pharmaceutically acceptable salt thereof, in water containing a dicarboxylic acid, or a salt thereof;
   (ii) freezing the water; and
   (iii) thereafter removing the frozen water under vacuum.

10. A lyophilisate according to claim 9, wherein NaOH is added in step (i).

11. A method for treating cancer in a patient comprising administering a reconstituted product of claim 4 to the patient, wherein the cancer being treated is breast cancer, esophageal cancer, gastric cancer, gall bladder cancer, bile duct cancer, colon cancer, rectal cancer, liver cancer, pancreatic cancer, ovarian cancer, head and neck cancer, mesotheolioma cancer, stomach cancer, bowel cancer, lung cancer or colorectal cancer.

* * * * *